United States Patent
Georgiou et al.

(10) Patent No.: US 11,923,063 B2
(45) Date of Patent: Mar. 5, 2024

(54) ARTIFICIAL PANCREAS WITH NEURAL SIGNAL INPUT

(71) Applicant: IMPERIAL COLLEGE OF SCIENCE, TECHNOLOGY AND MEDICINE, London (GB)

(72) Inventors: Pantelis Georgiou, London (GB); Amparo Güemes Gonzalez, London (GB); Pau Herrero-Viñas, London (GB)

(73) Assignee: Imperial College Innovations Limited, London (GB)

(*) Notice: Subject to any disclaimer, the term of this patent is extended or adjusted under 35 U.S.C. 154(b) by 0 days.

(21) Appl. No.: 17/050,677

(22) PCT Filed: Apr. 24, 2019

(86) PCT No.: PCT/EP2019/060535
§ 371 (c)(1),
(2) Date: Oct. 26, 2020

(87) PCT Pub. No.: WO2019/207007
PCT Pub. Date: Oct. 31, 2019

(65) Prior Publication Data
US 2021/0233637 A1 Jul. 29, 2021

(30) Foreign Application Priority Data
Apr. 24, 2018 (GB) .................................. 1806672

(51) Int. Cl.
G16H 20/17 (2018.01)
G16H 20/30 (2018.01)
(52) U.S. Cl.
CPC ............. *G16H 20/17* (2018.01); *G16H 20/30* (2018.01)

(58) Field of Classification Search
CPC ............................... G16H 20/17; G16H 20/30
(Continued)

(56) References Cited

U.S. PATENT DOCUMENTS 5,231,988 A * 8/1993 Wernicke ........... A61N 1/36053
607/2
2002/0026141 A1 2/2002 Houben et al.
(Continued)

FOREIGN PATENT DOCUMENTS

CN 105561431 A 5/2016
WO WO-9715227 A1 * 5/1997 ......... A61B 5/14532
WO WO-9746274 A1 12/1997

OTHER PUBLICATIONS

Low, Karen Gail; Remote-Activated Electrical Stimulation via Piezoelectric Scaffold System for Functional Nerve Regeneration ; University of California, Riverside. ProQuest Dissertations Publishing, 2017. 10633665. (Year: 2017).*
(Continued)

*Primary Examiner* — Hiep V Nguyen
(74) *Attorney, Agent, or Firm* — Harness, Dickey & Pierce, P.L.C.

(57) ABSTRACT

There is provided apparatus for controlling the delivery of insulin to a subject. The apparatus comprises a first input (18) for receiving neural information from the subject indicative of prospective or actual food and/or drink intake and a second input (15) for receiving a signal indicative of the subject's blood glucose level (BG). The apparatus further comprises a processor or processors (10) configured to determine food and/or drink characteristics based on the received neural information and to determine an amount of insulin to be delivered based on the measured blood glucose levels (BG) and the determined food and/or drink charac-
(Continued)

teristics, and an output for providing an insulin pump control signal (12) indicative of the determined amount of insulin.

11 Claims, 4 Drawing Sheets

(58) Field of Classification Search
USPC .............................................................. 705/2
See application file for complete search history.

(56) References Cited

U.S. PATENT DOCUMENTS

| 2010/0249889 | A1* | 9/2010 | Dobak, III | ........... | A61N 1/3615 |
| | | | | | 607/72 |
| 2013/0345772 | A1* | 12/2013 | Cholette | ................. | A61B 5/42 |
| | | | | | 607/40 |
| 2015/0073510 | A1 | 3/2015 | Perryman | | |
| 2019/0102523 | A1* | 4/2019 | Buckley | ................ | G06T 19/006 |

OTHER PUBLICATIONS

Muhammad Farooq et al. "A novel approach for food intake detection using electroglottography", Physiological Measurement, Institute of Physics Publishing, Bristol, GB, vol. 35, No. 5, Mar. 26, 2014.

* cited by examiner

ARTIFICIAL PANCREAS WITH NEURAL SIGNAL INPUT

TECHNICAL FIELD

The present invention relates to methods and apparatus for controlling insulin injection. In particular, though not necessarily, the present invention relates to a so-called artificial pancreas for controlling insulin injection and modulating insulin sensitivity without user input and using neural signal input.

BACKGROUND

Diabetes describes a group of metabolic diseases that affects an estimated 422 million people worldwide and that is predicted by the World Health Organization to become the seventh leading cause of death by 2030.

Type 1 diabetes is an autoimmune disease that destroys the pancreatic β-cells, so that insulin secretion is insufficient to control plasma glucose levels. An open-loop insulin delivery scheme has demonstrated good performance in reducing the hypoglycaemic periods, but it requires a lot of manual effort from the user and most subjects still have suboptimum glycaemic control [1].

Type 2 diabetes is characterised by chronic hyperglycaemia resulting from defects in insulin action, which leads to a reduction in insulin sensitivity and insulin resistance. As a result, to date many different approaches have been tried to modulate insulin sensitivity in these subjects with the goal of reversing the disease. Among them, nutritional and exercise approaches [2] and drug therapies oriented to take control over the inflammatory processes that underlie the insulin resistance [3] are the most widely studied treatments. However, none of them has optimal results [4].

Figure 1:
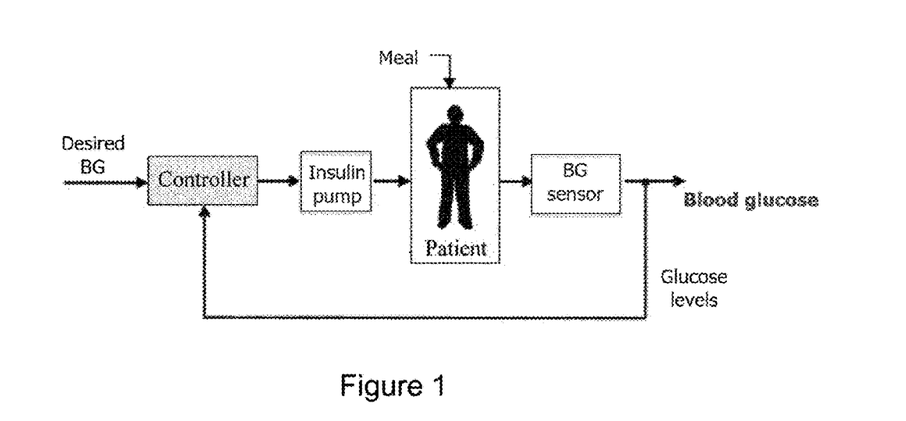
FIG. 1 illustrates schematically a known closed-loop insulin delivery system.

Therefore, systems that respond to changes in detected blood glucose concentrations by automatically modulating insulin delivery have been developed for managing both Type 1 and Type 2 diabetes. These systems are referred to as automated closed-loop insulin delivery systems, also known as Artificial Pancreases (APs), and they have shown improved glucose control and reduced risk of nocturnal hypoglycaemia when compared to previous techniques. A closed-loop insulin delivery system is illustrated schematically in FIG. 1, where "BG" is used to indicate "blood glucose".

However, some challenges, such as insulin delays during and following meals or the effects of exercising, still have to be resolved to achieve the best glycaemic control [1]. This is because the biological scenario in healthy subjects is very complex, and many biological substances, such as hormones and neurotransmitters, interact with each other to ensure a robust and tight regulation of the energy metabolism.

Figure 2:
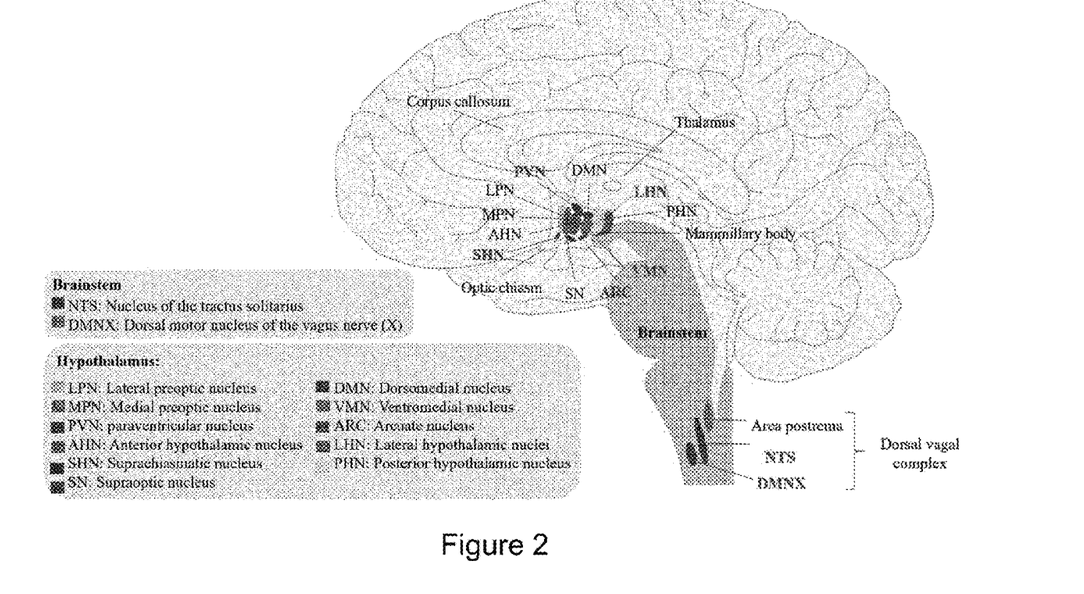
FIG. 2 illustrates areas of the brain most involved in glucose control.

In healthy subjects the brain, acting through the peripheral innervation to the different organs, has a crucial role in maintaining glucose homoeostasis. As such, the latest work in this field has been focused on revealing the underlying mechanisms by which the nervous system acts in glucose control, opening the door to a new perspective for studying both Type 1 and Type 2 diabetes [5, 6, 7]. FIG. 2 illustrates areas of the brain that are most involved in glucose control. Advances in technologies including this neural information may soon become a reality for the treatment of these endocrine diseases.

Further relevant publications include:

WO2018042147 which describes a method of adaptively determining one or more compensation factors in a closed-loop insulin delivery system comprising a continuous glucose level sensor; U.S. Pat. No. 5,231,988 which discloses stimulation of areas of the brain or the vagus nerve to re-duce the symptoms of Type 2 diabetes by modulating appetite, food intake and metabolic basal rate, initiating therapies based on information about meals, where the stimulation is initiated manually;

U.S. Pat. No. 6,922,590B1 which focuses on stimulation of the nucleus of the solitary tract (NTS); U.S. Pat. No. 7,440,806B1 and US0249421A1 which focus on electrically stimulating/inhibiting pancreatic secretion;

U.S. Pat. Nos. 5,188,104 and 5,263,480 which disclose systems that initiate therapies based on information about meals automatically at specified meal times or as a consequence of sensing food in the stomach or oesophagus (e.g. estimating amount of food by counting the number of swallows or the degree of stretching of the stomach); and CN105561431 which discloses an insulin injection control system that integrates brain wave detection from electroencephalogram (EEG) recordings into a glucose meter to improve the accuracy of blood glucose detection, whereby the EEG signal is used to calculate the proportion of glucose.

SUMMARY

It is an object of the present invention to be able to treat diseases such as Type 1 and Type 2 diabetes by means of an artificial pancreas that controls insulin injection and modulates insulin sensitivity without any user input, or with only minimal user input, and that optimizes treatment by exploiting recorded neural information.

According to a first aspect of the present invention there is provided apparatus for controlling the delivery of insulin to a subject. The apparatus comprises a first input for receiving neural information from the subject indicative of prospective or actual food and/or drink intake and a second input for receiving a signal indicative of the subject's blood glucose level. The apparatus further comprises a processor or processors configured to determine food and/or drink characteristics based on the received neural information, and to determine an amount of insulin to be delivered based on the measured blood glucose levels and the determined food and/or drink characteristics, and an output for providing an insulin pump control signal indicative of the determined amount of insulin.

The processor(s) may be configured to determine a characteristic of a neural stimulation signal to be applied by a neural stimulation unit, the apparatus comprising a further output for providing neural stimulation unit control signal indicative of said characteristic.

The apparatus may comprise a third input for receiving a signal indicative of a subject's insulin sensitivity, said processor(s) being configured to determine a characteristic of a neural stimulation signal to be applied by a neural stimulation unit using said signal indicative of a subject's insulin sensitivity.

The processor(s) may determine an amount of insulin to be delivered as one or both of a basal insulin dose or a meal bolus insulin dose.

The processor(s) may be configured to implement a learning mode in which signals received via said first input are classified according to the food and/or drink intake to which they relate and to store the results in a memory of the apparatus, the processor(s) being configured to determine food and/or drink characteristics based on a received neural information by analysing the signal and performing a look-up in said memory.

The apparatus may comprise one or more of an insulin pump connected or connectable to the first mentioned output; a body worn or implantable blood glucose sensor connected or connectable to said second input, and one or more body worn or implantable neural sensors connected or connectable to said first input.

The apparatus may comprise a body worn or implantable neural stimulation unit connected or connectable to said further output.

According to a second aspect of the present invention there is provided a method of controlling the delivery of insulin to a subject. The method comprises recording, using one or more body worn or implantable electrodes, neural information from the subject indicative of prospective or actual food and/or drink intake, and determining food and/or drink characteristics based on the recorded neural information. The method further comprises measuring the subject's blood glucose level using a body worn or implantable blood plasma glucose sensor, determining an amount of insulin to be delivered based on the measured blood glucose level and the determined food and/or drink characteristics, and providing a control signal indicative of the determined amount of insulin to an insulin pump to thereby deliver a required amount of insulin from the insulin pump to the subject.

The blood glucose sensor may be an implanted, subcutaneous blood glucose sensor.

The recording may be performed using one or more body worn electrodes configured to record neural signals.

The recording may be performed using one or more implanted electrodes configured to detect cephalic signals in efferent fibres in the vagus nerve to the pancreas and/or in afferent fibres in the vagus nerve from the stomach and/or to detect signals from afferent sympathetic nerves innervating a liver and/or brown adipose tissue and/or nuclei of hypothalamic areas.

The recording may be performed using one or more electrodes configured to monitor neural signals in the orbitofrontal cortex.

The method may comprise determining a characteristic of a neural stimulation signal to be applied to the subject and applying that signal to the subject via one or more body worn or implantable electrodes.

The method may comprise applying said signal to efferent sympathetic nerves to the liver and/or brown adipose tissue and/or hypothalamic areas to modulate insulin sensitivity.

The method may comprise recording, using one or more body worn or implantable electrodes, a neural signal indicative of the subject's insulin sensitivity, and determining said characteristic of a neural stimulation signal to be applied to the subject using said signal indicative of the subject's insulin sensitivity.

DETAILED DESCRIPTION

Figure 3:
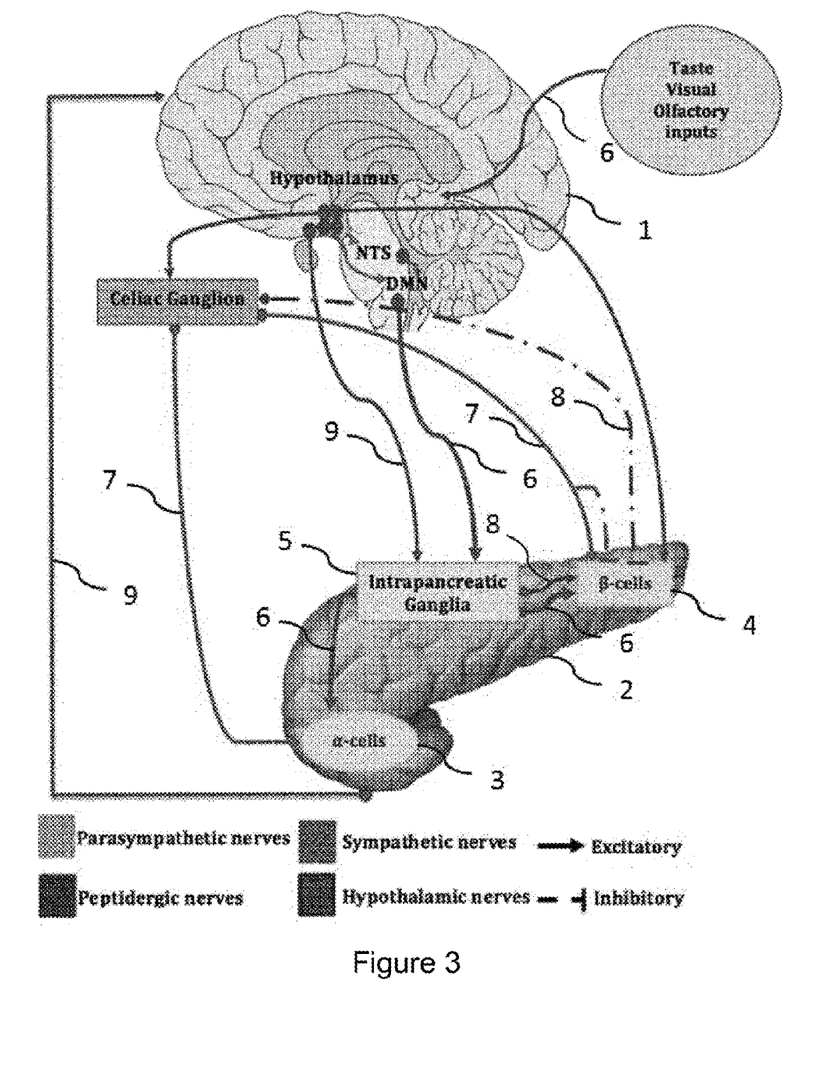
FIG. 3 illustrates schematically certain neural connections between the brain and the pancreas.

FIG. 3 illustrates schematically neural connections between the brain 1 and the pancreas 2, where the pancreas contains $\alpha$-cells 3, $\beta$-cells 4, and intrapancreatic ganglia 5. Note that the $\alpha$-cells which secrete glucagon, $\beta$-cells which secrete insulin, and intrapancreatic ganglia, though shown in separate regions in FIG. 3, are in reality distributed throughout the pancreas. The neural connections provide stimulation for these regions and include parasympathetic nerves 6, which stimulate insulin release, and sympathetic nerves 7, which can either stimulate or inhibit insulin release depending on the neurotransmitter receptor on the pancreatic cells to which the neurotransmitter binds. The neural connections also include peptidergic nerves 8 which can also stimulate insulin release and hypothalamic nerves 9 which are inhibitory of insulin secretion.

Figure 4:
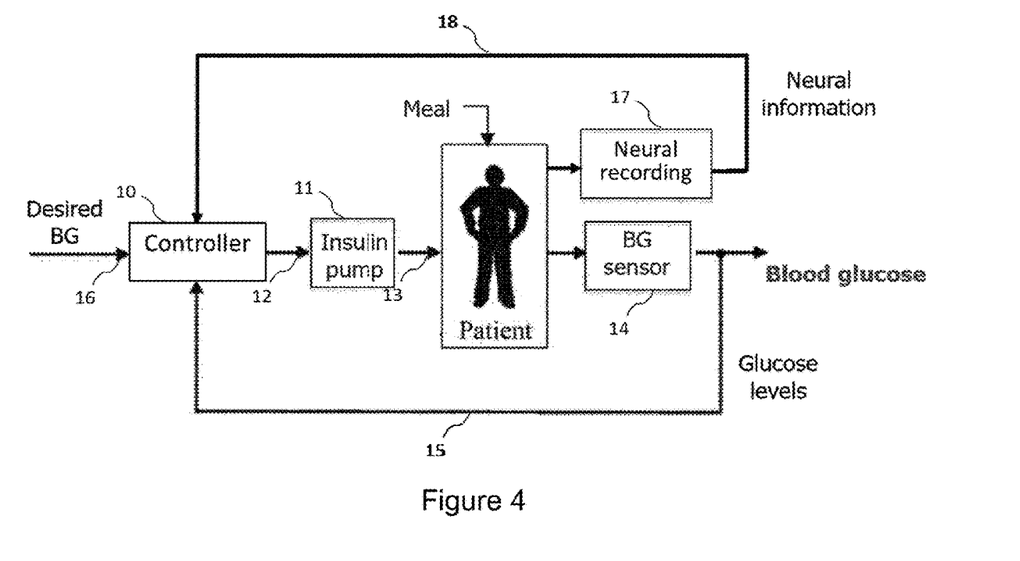
FIG. 4 illustrates an automated closed-loop system of insulin medication/delivery.

FIG. 4 illustrates schematically an improved, automated closed-loop system for insulin delivery that takes into account information from neural recordings, with the intention of requiring no, or minimal, intervention from the user, e.g. during meals, and which thus enables treatment and/or mitigation of at least Type 1 and 2 diabetes, and in particular episodes of hyperglycemia, hyperinsulinemia and hypoinsulinemia.

It will be appreciated that the system of FIG. 4 can be implemented using a novel combination of known components. Varying degrees of implantation within a subject's body are possible. However, one embodiment envisages a body worn controller 10 (CPU, memories, power supply, program code and data stored in memory) and a body worn insulin pump 11. The controller 10 provides at an output a control signal 12 that is fed to an input of the insulin pump (the communication link may be wired or wireless). The control signal drives the insulin pump to deliver a desired amount of insulin 13 via an implanted injection port (not shown). The system further comprises a subcutaneous blood glucose sensor 14 that detects a blood glucose level in the subject and feeds this back to a first input 15 of the controller (again via a wired or wireless link). The controller also receives at a second input 16 a signal defining a desired plasma (blood) glucose (BG) level that can be either pre-set or optimally calculated automatically based on the glucose levels and neural recordings (described below) that are measured. Although shown as an input to the controller, the BG level may be generated or stored internally within the controller.

A nerve signal sensor 17 is configured to record patterns of activation in the subject's nervous system. These may be indicative of preparation of the body for a meal intake (cephalic phase) and the characteristics of the meal (as perceived by the subject) and fed back to a third input 18 of the controller (once again via a wired or wireless link). Consequently, neural information and information regarding the blood glucose level in the subject can be used by the controller 10 to compute the optimal delivery of insulin/medication to the subject. The sensor 17 may comprise a body worn sensor such as an EEG sensor, or may comprise an implantable sensor.

Examples of sensors for recording neural information in the orbitofrontal cortex include: non-invasive EEG/MEG sensors, semi-invasive electrocorticography electrodes (ECoG) and invasive nano/microelectrode arrays located on the cortex to record field potentials.

Examples of sensors for recording neural information in the hypothalamus, particularly the arcuate nucleus, the ventromedial nucleus and the lateral hypothalamic nuclei, include invasive depth nano/microelectrode arrays.

Examples of sensors for recording neural information in the peripheral nerves, such as vagus efferent fibers to the pancreas and afferent fibers from the stomach, liver and brown adipose tissue (BAT), include chronically implanted bipolar cuff or split ring electrodes [17, 18]. The recordings might be performed either at the cervical, subesophageal or organ specific branch levels.

A high level of automated control of the glucose dynamics in the subject during meals is thus enabled, without the need for intervention by the subject in order to compute a meal bolus, which is the current restrictive and error-prone approach. In addition, inclusion of the neural information indicative the state of a subject's body allows optimization of the infusion of basal insulin.

Figure 5:
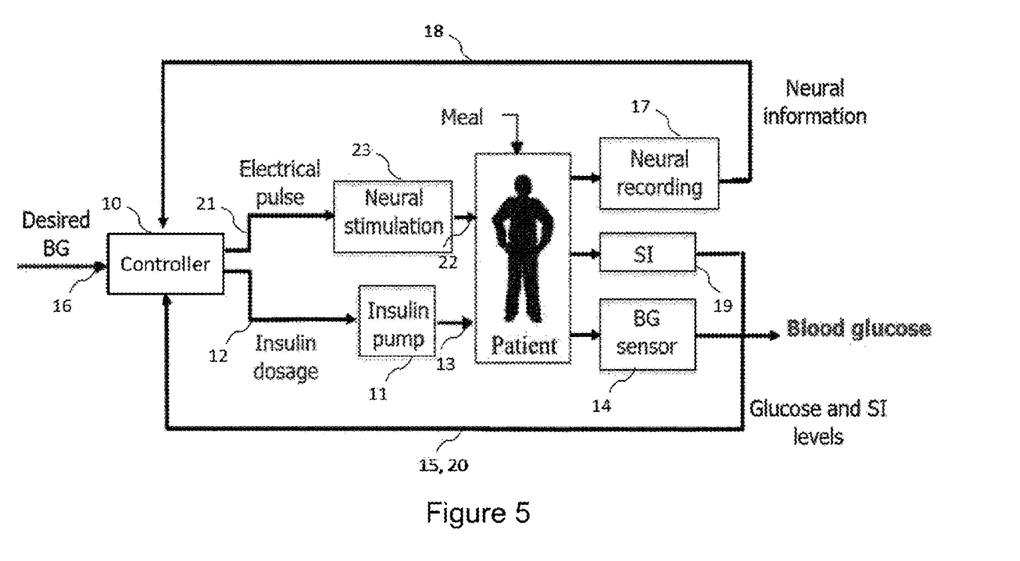
FIG. 5 illustrates an automated closed-loop system of insulin medication/delivery.

FIG. 5 illustrates schematically another example of an automated closed-loop system of insulin delivery that takes into account information from neural recordings and which requires no, or minimal, intervention from the user. In addition to the components of the system shown in FIG. 4, the system of FIG. 5 includes a sensor 19 configured to monitor insulin sensitivity (SI) and feedback a corresponding value to an input 20 of the controller 10. SI is a parameter that describes the effect that insulin has in the tissues, notably the liver where insulin inhibits hepatic glucose production and in other peripheral tissues where insulin promotes glucose uptake. Low insulin sensitivity is a sign of insulin resistance (Type 2 diabetes). Different hypothalamic areas, particularly the arcuate nucleus, the ventromedial nucleus and the lateral hypothalamic nuclei, and peripheral nerves have been established as potential targets for stimulation of insulin sensitivity [8].

The controller 10 is configured to provide, via an output, a signal 21 to an input of a neural stimulation unit 23. This unit, which may be body worn or implanted, provides stimulation signals 22, via electrodes (not shown), to the subject's nervous system. Examples of electrodes for stimulating the hypothalamic areas, particularly the arcuate nucleus, the ventromedial nucleus and the lateral hypothalamic nuclei, include invasive depth stimulation nano/microelectrode arrays. Examples of electrodes for stimulating peripheral nerves, such as vagus efferent fibers to the pancreas and afferent fibers from the stomach, liver and BAT, include chronically implanted bipolar cuff or split ring electrodes [17, 18] and non-invasive nerve stimulation systems such as eTNS, Parasym, gammaCore.

The unit may comprise a pulse generator powered by at least one battery.

The stimulation unit 23 may in some cases be integrated with the nerve signal sensor 17. The addition of the sensor 17 to monitor insulin activity in the body enables the controller 10 to compute a required electrical pulse stimulus and deliver this via the neural stimulation unit 23, to increase or decrease the subject's insulin sensitivity (i.e. effect of insulin) during infusion.

Figure 6:
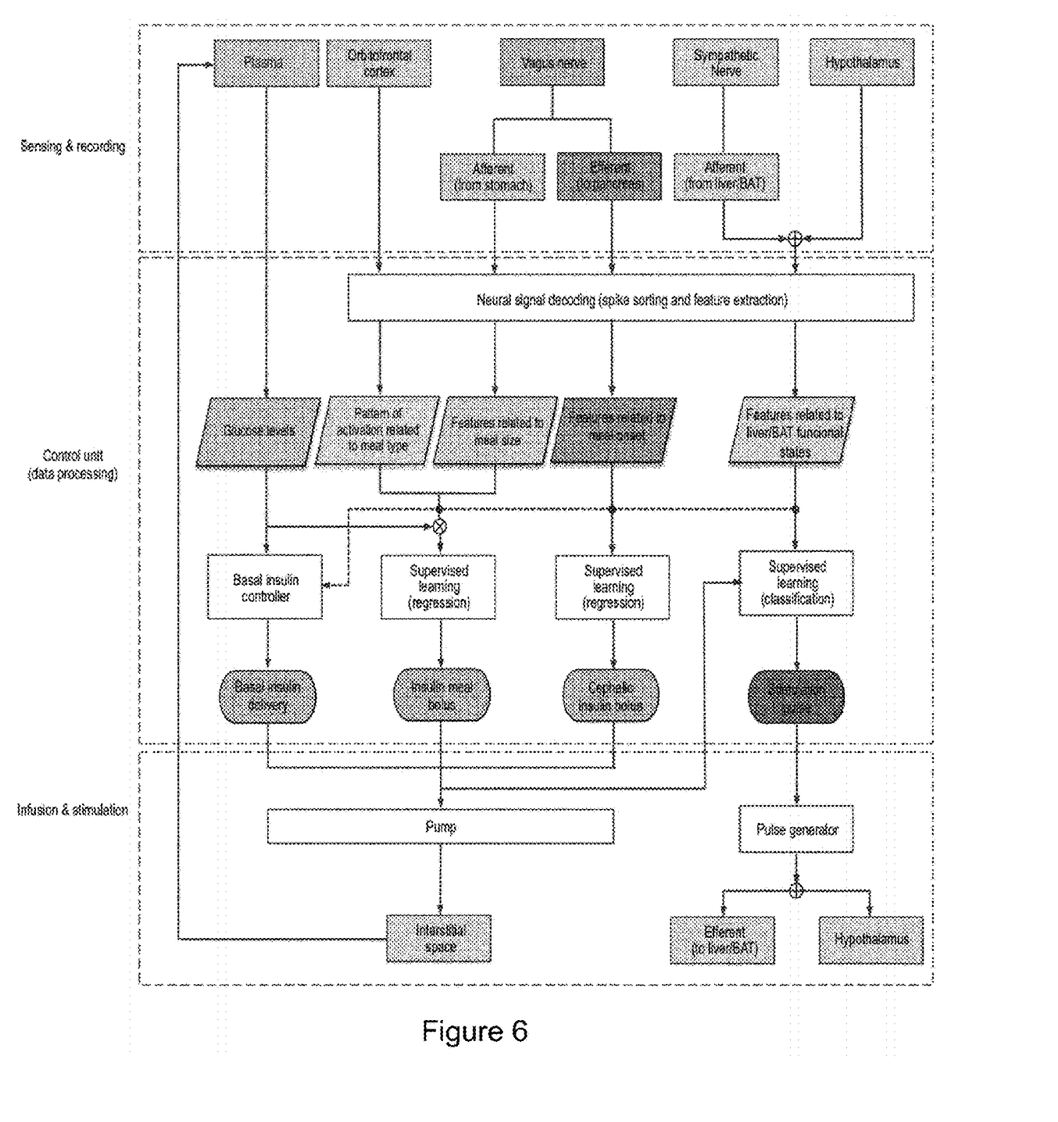
FIG. 6 illustrates the functional operation of the proposed device.

FIG. 6 illustrates the functional configuration of the system of FIG. 5, split into three components, namely (i) sensing and recording, (ii) data processing, and (iii) delivery and stimulation. These are considered separately in the following subsections.

(i) Sensing and Recording

As discussed, two principal variables are measured: plasma glucose and neural signals. Plasma glucose is continuously monitored (every 5 min) using glucose sensors known in the art (continuous glucose monitoring systems). Neural recordings are collected from different locations, centrally and peripherally, depending on the information to be obtained. All neural signals are continuously recorded.

A meal onset may be detected by recording the cephalic signals (i.e. before meal intake) in efferent fibres in the vagus nerve to the pancreas (either at the cervical, suboesophageal or pancreatic branch levels of the vagus nerve) [9, 10] using one or more recording electrodes. The amount of food being ingested may be assessed by collecting the afferent signals in afferent fibres of the vagus nerve from the stomach (recordings can be done at different levels of the vagus nerve) [11] using one or more recording electrodes. These signals encode information about the stretching of the stomach, which can then be related to meal size.

The type of food being ingested is related to the pattern of activation of neurons in the orbitofrontal cortex (prefrontal cortex region in the frontal lobes in the brain). Neurons in this region of the cortex respond to taste, olfactory and visual stimuli and are considered a convergence area of these systems [12, 13, 14, 15]. In addition, satiety reduces the neural activation in this area, which can be used as a signal of meal termination [16]. For this reason, recordings in this area provide a great amount of information about the meal type in all its "dimensions" (taste, color and odour).

Invasive recordings using deep electrodes may be required, but non-invasive measurements using EEG may be sufficient to provide the required information.

Signals from afferent sympathetic nerves innervating the liver and BAT and/or nuclei of the hypothalamus may be recorded using one or more electrodes in order to determine insulin sensitivity.

(ii) Data Processing

The neural recordings, especially those obtained from afferent nerves, carry information about the body's state. Therefore, their inclusion as inputs to the basal insulin controller, along with the measured blood glucose level, may allow an optimization of the infusion of insulin in the basal state. In addition, during meals, this information from neural recordings is of great value to achieve the best control of SI and optimally compute the insulin bolus to be delivered with the pump.

The first step in processing the neural recordings is to decode them, which may include spike sorting and feature extraction for each signal (similar to what it is currently done in brain-machine interface (BMI) systems). Signals may be analysed in parallel. A second step is to apply machine learning algorithms, such as supervised learning algorithms, to obtain the underlying structure of all the data and create a mapping with the variable of interest in each case.

Specifically, classification algorithms may be used for determining, on a binary basis (i.e. true or false), meal initiation from the efferent vagal signals that are sent to the pancreas during the cephalic phase. The features related to meal type and size (acquired from recordings in the orbitofrontal cortex and afferent vagal fibers from the stomach) and glucose levels may be used as an input to regression methods that assign to each specific set of features a value of insulin meal bolus to be delivered.

For each subject, the regression algorithm may be first trained to create a personalized mapping among the input variables and the output (insulin bolus). Then, once a representative set of data has been analysed, the insulin bolus that best matches the entries is selected. The same idea may be applied to determine the characteristics of the electrical stimulus to be applied given the insulin that is being delivered and the information regarding the states of the liver and BAT. The training step in all the supervised learning algorithms allows customization of the stimulus and the insulin delivery to each subject.

(iii) Delivery and Stimulation

The stimulus is delivered by the neural stimulation unit including one or more electrodes and one or more pulse generators/stimulators (likely implanted). The pulse parameters are determined based on the neural recordings as previously specified, in a closed-loop manner. The parameters include at least some of pulse width, output current or voltage, frequency, on time and off time. Stimulus is configured to prevent accommodation (i.e. a loss of sensitivity or habituation). Sites of stimulation include efferent sympathetic nerves to the liver/BAT and/or the same recording hypothalamic areas used for recording.

Stimulation in the hypothalamic areas and sympathetic nerves may be switched on only during meal intake. Meal intake is determined from the meal information encoded in neural signals acquired from the previously mentioned neural recordings and from the glucose levels. Accordingly, power consumption by the system may be optimized.

REFERENCES

[1] A. Haidar, L. Legault, V. Messier, T. M. Mitre, C. Leroux and R. Rabasa-Lhoret, "Comparison of dual-hormone artificial pancreas, single-hormone artificial pancreas, and conventional insulin pump therapy for glycaemic control in subjects with type 1 diabetes: an open-label randomised controlled crossover trial," The lancet Diabetes & endocrinology, vol. 3, no. 1, pp. 17-26, 2015.
[2] M. O. Weickert, "Nutritional modulation of insulin resistance," Scientifica, vol. 2012, 2012.
[3] R. Lamb and B. Goldstein, "Modulating an oxidative-inflammatory cascade: potential new treatment strategy for improving glucose metabolism, insulin resistance, and vascular function," International journal of clinical practice, vol. 62, no. 7, pp. 1087-1095, 2008.
[4] Z.-g. Gao and J.-p. Ye, "Why do anti-inflammatory therapies fail to improve insulin sensitivity?" Acta Pharmacologica Sinica, vol. 33, no. 2, pp. 182-188, 2012.
[5] R. Chandra and R. A. Liddle, "Recent advances in the regulation of pancreatic secretion," Current opinion in gastroenterology, vol. 30, no. 5, p. 490, 2014.
[6] R. Rodriguez-Diaz and A. Caicedo, "Neural control of the endocrine pancreas," Best Practice & Research Clinical Endocrinology & Metabolism, vol. 28, no. 5, pp. 745-756, 2014.
[7] W. Rosario, I. Singh, A. Wautlet, C. Patterson, J. Flak, T. C. Becker, A. Ali, N. Tamarina, L. H. Philipson, L. W. Enquist, et al., "The brain-to-pancreatic islet neuronal map reveals differential glucose regulation from distinct hypothalamic regions," Diabetes, vol. 65, no. 9, pp. 2711-2723, 2016.
[8] J. Ruud, S. M. Steculorum and J. C Brüning. Neuronal control of peripheral insulin sensitivity and glucose metabolism. Nature Communications, 8:ncomms15259, 2017.
[9] C. Simon, J. L. Schlienger, R. Sapin and M. Imler. Cephalic phase insulin secretion in relation to food presentation in normal and overweight subjects. Physiology & Behavior, 36(3):465-469, January 1986.
[10] B. Ahrén and J. J. Holst. The cephalic insulin response to meal ingestion in humans is dependent on both cholinergic and noncholinergic mechanisms and is important for postprandial glycemia. Diabetes, 50(5):1030-8, May 2001.
[11] G. J. Schwartz and T. H. Moran. Sub-diaphragmatic vagal afferent integration of meal-related gastrointestinal signals. Neuroscience & Biobehavioral Reviews, 20(1): 47-56, January 1996.
[12] Edmund T. Rolls. The functions of the orbitofrontal cortex. Brain and Cognition, 55(1):11-29, June 2004.
[13] P. A. M. Smeets, L. Charbonnier, F. van Meer, L. N. van der Laan and M. S. Spetter. Food-induced brain responses and eating behaviour. Proceedings of the Nutrition Society, 71(04):511-520, November 2012.
[14] I. E. de Araujo. Representation in the human brain of food texture and oral fat. Journal of Neuroscience, 24(12): 3086-3093, April 2004.
[15] E. T. Rolls and L. L. Baylis. Gustatory, olfactory, and visual convergence within the primate orbitofrontal cortex. The Journal of Neuroscience: The Official Journal of the Society for Neuroscience, 14(9):5437-52, September 1994.
[16] E. T. Rolls. Taste, olfactory, and food texture processing in the brain, and the control of food intake. Physiology & Behavior, 85(1):45-56, May 2005.
[17] Loeb, G. E., & Peck, R. A. (1996). Cuff electrodes for chronic stimulation and recording of peripheral nerve activity. Journal of Neuroscience Methods, 64(1), 95-103. https://doi.org/10.1016/0165-0270(95)00123-9
[18] Lee, S., Sheshadri, S., Xiang, Z., Delgado-Martinez, I., Xue, N., Sun, T., . . . Lee, C. (2017). Selective stimulation and neural recording on peripheral nerves using flexible split ring electrodes. Sensors and Actuators, B: Chemical, 242, 1165-1170. https://doi.org/10.1016/j.snb.2016.09.127

The invention claimed is:

1. Apparatus for controlling the delivery of insulin to a subject and comprising:
   a first input for receiving neural information recorded from the subject's nervous system and indicative of prospective or actual food and/or drink intake;
   a second input for receiving a signal indicative of the subject's blood glucose level;
   a processor or processors configured to determine food and/or drink characteristics based on the received neural information, determine an amount of insulin to be delivered based on the measured blood glucose levels and the determined food and/or drink characteristics, and output an insulin pump control signal indicative of the determined amount of insulin; and
   a third input for receiving a neural signal recorded from the subject's nerves innervating the liver and/or brown adipose tissue and/or nuclei of the hypothalamus indicative of a subject's insulin sensitivity;
   said processor(s) being configured to determine a characteristic of a neural stimulation signal to be applied by a neural stimulation unit using said signal indicative of a subject's insulin sensitivity, and the apparatus comprising a second output for providing neural stimulation unit control signal indicative of said characteristic; and
   said neural stimulation unit being configured to apply said neural stimulation signal to efferent sympathetic nerves to the liver and/or brown adipose tissue and/or hypothalamic areas in order to increase or decrease the subject's insulin sensitivity during delivery of the determined amount of insulin.

2. Apparatus according to claim 1, wherein the processor(s) are configured to determine an amount of insulin to be delivered as one or both of a basal insulin dose or a meal bolus insulin dose.

3. Apparatus according to claim 1, said processor(s) being configured to implement a learning mode in which signals received via said first input are classified according to the food and/or drink intake to which they relate and to store the results in a memory of the apparatus, the processor(s) being configured to determine food and/or drink characteristics based on a received neural information by analysing the signal and performing a look-up in said memory.

4. Apparatus according to claim 1 and comprising one or more of:
- an insulin pump connected or connectable to receive the insulin pump control signal;
- a body worn or implantable blood glucose sensor connected or connectable to said second input; and
- one or more body worn or implantable neural sensors connected or connectable to said first input.

5. Apparatus according to claim 4 wherein said neural stimulation unit comprises a body worn or implantable neural stimulation unit connected or connectable to said output.

6. Apparatus according to claim 1, said processor(s) being configured to implement a learning mode in which signals received via said third input are mapped to said characteristic of the neural stimulation signal to be applied by said one or more body worn or implantable electrodes, and the characteristic of the neural stimulation signal being at least one of an output current or voltage, pulse width, frequency, or on time and off time.

7. A method of controlling the delivery of insulin to a subject and comprising:
- recording, using one or more body worn or implantable electrodes, neural information from the subject's nervous system indicative of prospective or actual food and/or drink intake;
- determining food and/or drink characteristics based on the recorded neural information;
- measuring the subject's blood glucose level using a body worn or implantable blood plasma glucose sensor;
- determining an amount of insulin to be delivered based on the measured blood glucose level and the determined food and/or drink characteristics; and
- providing a control signal indicative of the determined amount of insulin to an insulin pump to thereby deliver a required amount of insulin from the insulin pump to the subject;
- recording, using one or more body worn or implantable electrodes, a neural signal from nerves innervating the liver and/or brown adipose tissue and/or nuclei of the hypothalamus indicative of the subject's insulin sensitivity;
- determining a characteristic of a neural stimulation signal to be applied to the subject using said neural signal indicative of the subject's insulin sensitivity; and
- applying that stimulation signal to the subject's efferent sympathetic nerves to the liver and/or brown adipose tissue and/or hypothalamic areas via one or more body worn or implantable electrodes in order to increase or decrease the subject's insulin sensitivity during delivery of the determined amount of insulin.

8. A method according to claim 7, wherein said blood glucose sensor is an implanted, subcutaneous blood glucose sensor.

9. A method according to claim 7, wherein said recording is performed using one or more body worn electrodes configured to record neural signals.

10. A method according to claim 7, wherein said recording of neural information from the subject's nervous system indicative of prospective or actual food and/or drink intake is performed using one or more implanted electrodes configured to detect cephalic signals in efferent fibres in the vagus nerve to the pancreas and/or in afferent fibres in the vagus nerve from the stomach and/or to detect signals indicative of insulin sensitivity from afferent sympathetic nerves innervating a liver and/or brown adipose tissue and/or nuclei of hypothalamic areas.

11. A method according to claim 7, wherein said recording of neural information from the subject's nervous system indicative of prospective or actual food and/or drink intake is performed using one or more electrodes configured to monitor neural signals in the orbitofrontal cortex.

* * * * *